United States Patent [19]

Cohen et al.

[11] Patent Number: 5,607,842
[45] Date of Patent: Mar. 4, 1997

[54] USE OF TRNA GENES TO STABILIZE THE INHERITANCE OF UNSTABLE PLASMIDS IN POPULATIONS OF GROWING CELLS

[75] Inventors: Stanley N. Cohen, Portola Valley, Calif.; Martin Vögtli, Lenzburg, Switzerland

[73] Assignee: The Board of Trustees of the Leland Stanford Junior University, Stanford, Calif.

[21] Appl. No.: 230,427

[22] Filed: Apr. 19, 1994

Related U.S. Application Data

[63] Continuation of Ser. No. 955,982, Oct. 2, 1992, abandoned.

[51] Int. Cl.[6] .............................. C12P 21/02; C12N 1/21; C12N 15/70; C12N 15/74
[52] U.S. Cl. ................ 435/69.1; 435/252.3; 435/252.33; 435/320.1
[58] Field of Search ............................... 435/69.1, 172.1, 435/172.3, 252.3, 252.35, 320.1, 252.33; 536/23.2, 23.4, 24.1; 935/24, 27, 29, 38, 39, 25

[56] References Cited

U.S. PATENT DOCUMENTS 4,752,577  6/1988  Belagaje et al. ...................... 435/69.4
5,059,529  10/1991  Oppenheim et al. .................. 435/69.4

OTHER PUBLICATIONS

Reiter, et al. (1989) Nucleic Acid Research 17:1907–1914.
Vogtli and Cohen (1992) Molecular Microbiology 6:3041–3050.
Vold (1985) Microb. Reviews 49:71–80.
Fournier and Ozeki (1985) Microb. Reviews 49:379–397.
Sedimeier and Schmeiger (1990) Nucleic Acid Research 18:4027.
Plohl and Gamulin (1990) Mol. Gen. Genet. 222:129–134.
Gamulin and Soll (1987) Nucleic Acid Research 15:6747.
Sprinzl, et al. (1991) Nucleic Acid Research 19 (suppl):2127–2171.
Weissharr, et al. (1990) Nucleic Acid Research 18:1902.
Hollingworth and Hallick (1982) J. Biol. Chem. 257:12795–12799.
Goodman, et al. (1970) Eur. J. Biochem. 13:461–483.
Pierson and Kahn (1987) J. Mol. Bio. 196:487–496.
Brown, et al. (1990) J. Bacteriol. 172:1877–1888.
Sosio, et al. (1989) Mol. Gen Genet. 218:169–176.
Omer and Cohen (1989) SLP1: A paradigm for plasmids that site-specifically integrate in the Actinomycetes in Mobile DNA, eds. Berg and Howe, American Society for Microbiology, pp. 289–296.
Boccard, et al. (1989) Plasmid 21:59–70.
Omer and Cohen (1986) J. Bacteriol. 166:999–1006.
Grunstein et al. (1975) Proceeding of the National Academy of Sciences, vol. 72, pp. 3961–3965.
Shatzman et al. (1987) in Methods in Enzymology (Academic Press, San Diego), vol. 152, pp. 661–673.
van Delft et al. (1987) Nucleic Acids Research, vol. 15, pp. 9515–9530.
Rokem et al. (1990) Nucleic Acids Research, vol. 18, p. 3988.

*Primary Examiner*—James S. Ketter
*Attorney, Agent, or Firm*—Bertram I. Rowland

[57] ABSTRACT

Expression systems are provided, where plasmids can be safely maintained in a prokaryotic host, by providing for a tRNA gene for an essential tRNA in a tRNA gene negative background. A non-selective medium can be employed to permit vigorous growth of the host and efficient expression of a protein of interest.

14 Claims, 6 Drawing Sheets

```
        SalI
  1  GTCGACCTTCCTGCCGCTCGAGACGATGTCGAAACTGGAGTCGGCCATGTCCTG    60
 61  TGGCTCCTTGTATCTGGGCCGTGTCGGGCCGGTATCGGGTCCGTACCGGCATACGTCG  120
121  GCGGCCGCCCGGCCCCGCGGGGTCCTCGGCCGCCATCCGGACAAGCCTAGCCACCCGCGT 180
181  GATCCGAGCGGGCGATCAATCGGTGGGCGAAGCACCCCTCCGCATCAGGTATTGTTTACGT 240
241  CGTTGCCACGGAGCGCCGAAGAGCGGTTCGACGAGCAGCAAACCCCGGGCGGTGTGCC   300
        AvaI
301  CGAGCGGGCCAAAGGGAGCAGACTGTAAATCTGCCGGCCTTCCCAGGTTCGAATCC    360
        NarI                                     XhoII
361  TGGCGCGCCACACGACCGAAAGGTCTGTGACCAGCAATGCTGATCACAGACCCTT    420
421  TCGTGTCGTTCTCGGTGCCCACGGGATCTCGGGTTCTCTGCCCTTGCCCACGGTGTACGCG 480
```

FIG. 3A

```
481  GGATCATGTCCCGTGCTCCACGTTGTGAGCGTCAGGGGATTCGGGGCAGCGGTGACCGA  540
541  CACCACGCAACGTATCTTTCTCAGCTACGCAGCCCGGACCAGGCCTGGGCGGAGTGGGC  600
601  CGGCTGGCAGCTCCAGCAGGCCGGGCACCAGGTCGAGCTGGACCGGTGGCACTGGCCAC  660
661  CGGTGACGACTTCGTCCAGAAGATGAACCTGGCTCTCGGCAAGCCGACGCGGTGGTGGC  720
721  CCTGTTCTCCAGGCACTACTTTGAGCCCAAACGATGACCAGGAAGAGTGGTCGGCCGC  780
                                NarI              PvuI
781  CGTGGCCCTGCGCGGGGGCCCTCGTTCCGGTAGGATCGAGCTCCTGAACGACGACGACAT  840
841  CCCCGCCCTGCTGGCCCGGGACACTGCGCACAGACGTTCACGGGCTGGACGAGGCCGC  900
                                                          SalI
901  CACTTCTGCCCTGCTCGAAGCCGTCCACGGACCGGTTCCCCCTACCGGTCCGGTCGAC  958
```

USE OF TRNA GENES TO STABILIZE THE INHERITANCE OF UNSTABLE PLASMIDS IN POPULATIONS OF GROWING CELLS

This application is a continuation of application Ser. No. 07/955,982, filed 02 Oct. 1992, now abandoned.

INTRODUCTION

1. Technical Field

The field of this invention concerns the maintenance of extrachromosomal elements in prokaryotic organisms.

2. Background

Genetic engineering has allowed the discovery of numerous structural genes from a wide variety of sources, as well as the ability to mutate such naturally-occurring structural genes and to synthesize novel genes. For structural genes to find use commercially, it is necessary that there be an efficient expression system to allow for high yields of the protein in a readily-purifiable form. Depending upon the protein of interest, the characteristics of the expression host may be narrowly circumscribed. Desirably, the host should stably maintain the extrachromosomal element, grow rapidly and have relatively inexpensive growth medium, be free of toxins and other adventitious agents which may contaminate the product, and be able to produce the protein product in high yield and desirably in a functional form or having the capability of being readily functionalized to an active product.

In many situations it may be desirable to maintain the structural gene on an extrachromosomal element, rather than have it integrated into the genome. Integration into the genome may not be feasible or may result in rearrangements of the structural gene, loss of part or all of the structural gene, or other problems such as mutational alteration of the chromosomal site into which the gene is inserted. Particularly, the structural gene may be lost while the selective marker may be retained, since uncoupling between the structural gene of interest and the selected marker will be more pronounced in the chromosome than in a plasmid. Additionally, maintenance of two structural genes extrachromosomally allows multiple copies of the gene to exist within the same cell, increasing production of the product encoded by the gene.

It is therefor of interest to develop expression systems which allow for stable maintenance of extrachromosomal elements and provide for substantial efficiencies in producing an expression product from an exogenous host. Commonly this is accomplished by including an antibiotic resistance gene on two extrachromosomal elements and concurrently employing growth media that contains the appropriate antibiotic; alternatively, a gene encoding a nutritional requirement can be included on an extrachromosomal element introduced into a cell mutated in that gene. When this is done the host must be grown in specialized media deficient for the required nutrient. Finally, genes that kill the host when another gene is lacking have been identified and have been used to accomplish the stable inheritance of extrachromosomal elements in hosts that carry a kill-override gene in their chromosome; however, this approach seems to be restricted to certain species of hosts.

Relevant Literature

Reiter, et al. (1989) *Nucleic Acids Res.* 17, 1907–1914; Omer and Cohen (1986) *J. Bacteriol.* 166, 999–1006; and Omer and Cohen (1989) SLP1: A paradigm for plasmids that site-specifically integrate in the *Actinomycetes*. In *Mobile DNA*. Berg, D. E., and Howe, M. M. (eds). Washington, D.C. American Society for Microbiology, pp. 289–296 report that DNA sequences published for the att sites of SPL1 and certain other genetic elements integrate site-specifically into bacterial chromosomes having the characteristics of tRNA coding sequences. For SPL1, the integration site resembles a tRNA$^{Tyr}$ coding sequence. Similar inferences have been made from DNA sequence analyses of the chromosomal attachment sites of other plasmids of the actinomycetes (Boccard, et al. (1989) *Plasmid* 21, 59–70; Sosio, et al. (1989) *Mol. Gen. Genet.* 218, 169–176; and Brown, et al. (1990) *J. Bacteriol.* 172, 1877–1888) and the bacteriophages P4 and P22 of *E. coli* and *Salmonella typhimurium*, respectively (Pierson and Kahn, (1987) *J. Mol. Biol.* 196,487–496). These reports lack experimental evidence to indicate that the integration sites for these extrachromosomal genetic elements are actual functional tRNA genes.

The sequence of tRNA$^{Tyr}$ genes from a variety of different species has been reported by Goodman, et al. (1970) *Eur. J. Biochem.* 13, 461–483; Hollingsworth and Hallick, (1982) *J. Biol. Chem.* 257, 12795–12799; and Weisshaar, et al. (1990) *Nucleic Acids Res.* 18, 1902. The structural tRNA genes of widely diversified biological species are highly conserved (Sprinzl, et al. (1991) *Nucleic Acids Res.* 19 (Suppl.), 2127–2171). Many tRNA's are redundant in Streptomyces (Gamulin and Soll (1987) *Nucleic Acids Res.* 15, 6747; Plohl and Gamulin (1990) *Mol. Gen. Genet.* 222, 129–134; and Sedimeier and Schmieger (1990) *Nucleic Acids Res.* 18, 4027) and other prokaryotic organisms (see Fournier and Ozeki (1985) *Microbiol. Rev.* 49, 379–397 and Vold (1985) ibid 49, 71–80).

SUMMARY OF THE INVENTION

Compositions and methods are provided for stable extrachromosomal expression systems employing tRNA-minus (tRNA$^-$) prokaryotic hosts, where the tRNA$^-$ is an essential tRNA, comprising a plasmid that contains the complementing tRNA gene. Particularly, tRNA$^-$ prokaryotic hosts which have a plasmid containing a functional complementary tRNA$^{aa}$ gene capable of transcription and an exogenous structural gene of interest capable of expression in the host are grown in a non-selective medium, where the product is produced in high yield and with enhanced efficiency.

BRIEF DESCRIPTION OF THE FIGURES

3

FIG. 5 is a map of plasmid pMOV203 and derived constructs. The segments of Streptomyces origin are boxed for the pIJ101 replicon and indicated by an open arrow for the hyg gene. Amp: ampicillin resistance gene. Map positions for SphI, BamHI, and PstI are indicated. The length of specific plasmid DNA segments is shown. Plasmids pMOV204 to pMOV208 were constructed by BamHI linker-directed introduction of DNA fragments into the single BamHI site of pMOV203; these fragments were: 958 bp SalI (pos. 1)—SalI (pos. 953) for pMOV204 and pMOV208, 442 bp SalI (pos. 1)—XhoII (pos. 442) for pMOV206 and pMOV207, and 750 bp SalI (pos. 1)—SalI (pos. 953), containing a Bal31-generated deletion of 210 bp, for pMOV205. The termini of the deletion of pMOV205 were mapped by restriction analysis to nucleotide position 260 and 470, respectively. The orientation of these fragments was such that the transcription direction of the tRNA gene was the same as for the hyg gene. Mutation of the tRNA gene in pMOV207 and pMOV208 introduces a PstI site that separates the gene into two fragments of indicated size (in bp). The position and direction of transcription of the structural tRNA gene are shown by an arrow above the indicated DNA fragments. Plasmid pMOV203 and its derived constructs have an estimated copy number of approximately 100 per genome.

DESCRIPTION OF THE SPECIFIC EMBODIMENTS

Methods and compositions are provided for efficient expression of exogenous proteins in a prokaryotic host. The method is characterized by employing a prokaryotic host which provides a negative background for an essential transfer RNA and a plasmid that contains a desired structural gene and whose stability is enhanced by the presence of a functional copy of the essential tRNA gene, and optionally a marker for selection. The method comprises growing the expression host containing the plasmid in a non-selective medium, whereby the plasmid is stably maintained and the expression host can grow without the deleterious effects of a selective agent.

A principal advantage of a tRNA gene over other genes used as markers which might be complementary to a negative background is that specialized selective growth media lacking one or more of a required nutrient or containing antibodies or other selective agents need not be employed. Additionally, it does not encode any protein having the potential to contaminate a desired product. In addition, it is not part of a polycistronic locus, so that its absence will not affect the level of expression of other genes.

A wide variety of expression hosts may be employed, particularly those hosts for which substantial experience exists in fermentation, particularly where the hosts have already been found useful for expression of exogenous proteins. Desirably, the hosts do not form toxins which may contaminate the proteinaceous product, particularly where the proteinaceous product may find use as a drug, in foods, or other situations where the product must find physiological acceptance.

The host is also characterized by lacking an essential tRNA gene. By essential it is intended that the gene is required for translation of one or more proteins needed for cell growth. By "lacking" it is intended that all cellular copies of the essential gene should be deleted or mutated. If mutated, the host should have a very low reversion rate to a functional tRNA, preferably lower than about $10^{10}$. The essential tRNA may vary from host to host and within a particular species. Desirably, to facilitate deletion or mutation of the essential gene, the host should have a low number of genes encoding for tRNAs for said amino acid, usually fewer than 6, preferably fewer than about 3.

The inactivation of the tRNA gene can be achieved in a variety of ways including homologous recombination involving deletions, insertions, substitutions, or combinations thereof, particularly deletions and insertions, by random mutation employing mutating agents and selection, where the tRNA may be provided exogenously during screening, followed by transformation with the plasmid, or by employing in vitro mutagenesis, where fragments of the genome may be transferred and cloned in another host, the tRNA gene mutated by any convenient means, e.g. deletion by restriction enzyme, or the like, and the mutated segment(s) introduced into the target organism. Desirably, expression hosts may be employed which have already been optimized for producing exogenous proteins, so that the sole significant change in the host will be the inactivation of the essential tRNA.

While desirably there will be only one tRNA gene for the particular amino acid, where there are a plurality of such genes, desirably not more than 3, those genes may be individually inactivated, so as to provide for a host which is negative as to the capability of providing the particular amino acid during expression.

When using homologous recombination to inactivate the tRNA gene, since the gene is essential, one must provide a plasmid which carries the essential tRNA gene. The deletion construct may exist as a separate DNA sequence, where it may be introduced into the host by any convenient means, where the construct will allow for selection of the deletion of the chromosomal copies tRNA gene. Desirably, one may provide for various means to distinguish between the tRNA gene on the plasmid and the chromosomal tRNA. This can be achieved, for example, by having a construct with homology substantially outside of the tRNA gene, that is, with the flanking regions of the tRNA gene; by replacing the native chromosomal tRNA gene with a tRNA gene which is integrated at a different site, which site allows for ready inactivation; by providing for tandem integration of the construct, which results in two copies of the tRNA gene and flanking regions, which may then be subject to random excision; and the like. The chromosomal changes may be monitored by any convenient means, such as PCR, restriction analysis, growing the cells where loss or curing of the cells of the plasmid would indicate retention of the chromosomal gene, or other convenient means.

A wide variety of organisms may be employed as the hosts, particularly those which have already been established for fermentation, more particularly those which have advantages, such as allowing for secretion; have plasmids which have been engineered specifically for use in such organisms; have low reversion frequencies to tRNA gene-positive background, and the like. One group of organisms of particular interest are the actinomycetes which include the family actinomycetaceae, which family includes the genera actinomyces and bifidobacterium; the family mycobacteriaceae, which includes the genus microbacterium; the family streptomyctaceae, which includes the genus streptomyces; and the family micronosporaceae, which includes the genera micromonospora and thermoactinomyces.

Species of particular interest include *S. lividans, S. coelicolor, S. fragea, S. griseofuscus, S. reticuli, S. remosus, S. albus, S. parvulus, S. ambfaciens, S. aurofaciens, S. plicatus, S. espenosus, S. incolnensis, S. erythresus, S. antibioticus, S. griseus, S. glanucens, S. kagagaens, s,. gegeirirensis, S. ghanaensis*, etc. Another group of organisms of interest are the endospore-forming bacteria, particularly the genus bacillus which includes species such as *B. subtilis, B. licheniformis, B. cereus, B. stearothermophilus*, and the like. Other organisms of interest include *Escherichia coli*, which has frequently been used for synthesis of the products of adventitious genes.

The plasmids which are employed will comprise an origin for replication, the tRNA gene essential for cell viability complementing the negative background in the host, at least one gene for expression of a protein of interest functional in said host for expression, optionally one or more genes for initial selection or other functional aspects, such as polylinkers for ease of insertion, specific sequences allowing for ease of PCR replication, specific restriction sites, and the like. Various origins may be employed having varying degrees of stability, where the origins may provide for single or multicopy plasmids. Descriptions of plasmid constructs including origins, promoters, enhancing elements, signal sequences, and the like are found in WP92/04452; JP3155790; WO90/10701; JP2002379; EP91/106268; WO88/07079; EP86/113627; EP85/103460; EP85/103461, Murakami, et al., *J. Bacteriol.* (1989) 171, 1459–1466; and Iwasaki, et al., *J. Antibiot* (Tokyo) (1986) 39, 985–993.

In addition, there are various replication systems which have specialized functions. Replication systems, described in U.S. Pat. No. 4,374,927 and Uhlin, et al. *Gene* (1979) 6, 91–106, provides for runaway replication, which can be initiated by an external agent, e.g. heat. In this manner, one may grow the expression host to high density, while avoiding expression of the structural gene of interest and then changing the temperature to the permissive temperature, allow for an expansion of the plasmid with concomitant expression of the structural gene. This can find particular application where the structural gene may be sensitive to degradation, is cytotoxic to the host, or may be subject to various modifications while being retained in the host. For the most part, the subject invention will be involved with plasmids, where for one reason or another, the available origins are low-copy-number and the plasmids do not segregate evenly upon mitosis, so that during continued culture in the absence of selection, the plasmids are lost from most cells in the population. The particular basis for the instability is not crucial to this invention.

The structural gene of interest may be any gene which produces a protein or antisense RNA. A "structural" gene is distinguished from non-structural genes which are only transcribed and not expressed. For the most part, the genes will be cDNA genes, lacking introns, although to the extent that the host has mechanisms for excising introns, intron-containing genes may also find application. The genes may express any protein of interest either exogenous to or endogenous to the host, normally being mammalian proteins, particularly primate, e.g. human, bovine, ovine, canine, equine, porcine, feline, or avian proteins. The proteins may be associated with hematopoiesis, such as colony-stimulating factors, interleukins, etc.; associated with clotting, such as tissue plasminogen activator, urokinase, streptokinase, Factor VIII c, von Willebrand's factor, Factor IX, Factor X, Factor XI, Christmas factor, fibrinogen, thrombin, etc.; adhesion molecules, such as L-selectin, E-selectin, LAF-1, integrins, such as VLA4, cutaneous lymphocyte adhesion molecule; hormones, such as growth hormone, somatostatin, somatotropin, insulin, etc.; interferons; enzymes, such as chymosin, proteases, particularly for surfactants, saccharidases, e.g. pectinases, amylases, endoglycosidases; nucleic acid formation enzymes, such as topoisomerases, gyrases, integrases, RNA polymerase, RNAse, other nucleases, DNA polymerase, etc.; viral proteins, such as envelope or capsid proteins of retroviruses, e.g. HTLV-I, -II, HIV, DNA viruses, CMV, adenovirus, papilloma virus, etc.; proteins of infectious unicellular organisms, e.g. Gram-negative bacteria, fungi, protista, etc.

The promoter for the structural gene may be any promoter which is functional in the host and may be constitutive or inducible. A wide variety of promoters are inducible, which may be used with advantage in the expression host. Illustrative inducible promoters include β-gal, metallothionein promoters, heat sensitive protein promoters, tetracycline resistance gene promoters, etc.

Expression may then be induced at an appropriate time when the expression host has reached the desired cell density. Any of a wide variety of convenient termination groups may be employed, conveniently ones that are native to the expression host. Thus, expression cassettes can be prepared, where the direction of transcription will comprise the transcription initiation region comprising the promoter and any other regulatory regions, such as enhancers, inducing regions, various response elements, followed by the open reading frames encoding the gene with an appropriate initiation codon, followed by a termination region, which comprises the stop codons, optionally a polyadenylation sequence, and a termination sequence. The promoter will be functional in the host and may be endogenous or exogenous.

A wide variety of agents which allow for selection are available, particularly antibiotics, such as neomycin, methotrexate, chloramphenicol, actinomycin, tetracycline, thiostrepton (tsr), heavy metals, and the like. A wide variety of genes are available which provide resistance to these various antibiotics or to the heavy metals, such as the metallothioneins.

The plasmid may be introduced into the host by any convenient means, such as calcium chloride treatment, electroporation, fusion, lipofection, etc.

Once the hosts have been transformed, they may be selected by the selective agent present on the plasmid or as a result of the presence of the essential tRNA on the plasmid, only the cells having the plasmid should be able to grow. However, where the cell still retains a chromosomal tRNA gene, it will be necessary to use the selective agent to select for those cells in which the plasmid is present.

The cells comprising the plasmid may be grown in accordance with conventional ways and be used to seed fermentations for production of the protein. The organisms can be grown in any convenient growth media, which may be supplemented as appropriate for the particular organism. A number of texts are available which describe media for different organisms. The subject invention provides the advantage that there need be no selective agent and therefore, the cells can enjoy vigorous growth.

The following examples are offered by way illustration and not by way limitation.

EXPERIMENTAL

Experimental Procedures

*S. lividans* TK21 (Hopwood et al. (1983) *J. Gen. Microbiol.* 129, 2257–2269) was used as the Streptomyces host. The generation of mutants from this strain is described in the text. Agar medium was R2YE; YEME was used for liquid cultures (Hopwood, et al. (1985) *Genetic Manipulation of Streptomyces*, A laboratory manual, Norwich, U.K., John Innes Foundation). Conditions for culture and transformation of Streptomyces were as described (Hopwood, et al. [1985]). *E. coli* DH10B and DH5αF' (GIBCO BRL) were grown on L-agar or in L-Broth at 37° C. (Miller (1972) *Experiments in molecular genetics*, Cold Spring Harbor, N.Y., Cold Spring Harbor Laboratory Press). Transformation of *E. coli* was as described (Hanahan (1985) *Techniques for transformation of E. coli*, In DNA cloning, volume 1, Glover, D. M. (ed), Oxford, U.K., IRL Press, pp.109–135). Plasmid pUC19 (Norrander, et al. (1983) *Gene* 26, 101–106) was the cloning vector in *E. coli*.

A list of the integration vectors used in gene replacement experiments is shown in Table 1.

TABLE 1

Integration vectors used in gene replacement experiments.

| Integration Vector | Selective Marker Gene | Chromosomal Target Site | Mutation | Extent of Homology (kb) |
|---|---|---|---|---|
| pMOV40 | tsr, hyg | afsR | hyg insertion | 5.3, 2.7 |
| PMOV71 | tsr | afsR | attB insertion | 5.5, 3.0 |
| pMOV75 | tsr | attB | attB deletion | 5.4, 2.1 |
| pMOV181 | hyg | afsR | dag insertion | 5.3, 2.7 |

The chromosomal locus targeted by each integration vector construct and the nature of the mutation generated are indicated. The extent of DNA homology between chromosome and integrating plasmid on either side of the insertion or deletion site is shown. Construction of the plasmids listed is described in detail in Experimental Procedures.

The plasmids used in these studies were constructed as follows: a 8.5 kb EcoRI/HindIII fragment that carries the SLP1 attB site cloned on pCAO109 (Omer and Cohen, 1986, supra) was inserted into pUC19. Into the unique HindIII site, a thiostrepton resistance gene (tsr) derived from pIJ6 (Kieser, et al. (1982) *Mol. Gen. Genet.* 185, 223–238) was inserted as a HindIII fragment to form pMOV72. Internal deletion of a 960 bp SalI fragment harboring the attB site generated pMOV75. A previously cloned afsR-complementing DNA segment from *S. lividans* (Omer, et al. (1988) *J. Bacteriol.* 170, 2174–2184) was subcloned as a 8.7 kb EcoRI/BamHI fragment from pBE5 (Stein and Cohen (1989) *J. Bacteriol.* 171, 2258–2261) onto pUC19 to form pBE1. The tsr gene was inserted as a 1.05 kb BclI fragment into the single BamHI site. Plasmid pMOV71 was formed by inserting a 960 bp attB-containing DNA fragment into a single BamHI site that was generated by linker insertion into one of the two SphI sites within the insert DNA. To form pMOV40, pBE1 was linearized by partial cleavage with SphI and treated with Bal31. The generated ends were ligated to KpnI linkers and the DNA fragments recircularized. A plasmid with an introduced deletion of 500 bp was selected, and a hygromycin resistance gene (hyg) derived from pFM4 (Malpartida et al. (1983) *Biochem. Biophys. Res. Comm.* 117, 6–12) was inserted as a 1.45 kb Asp718 fragment into the newly introduced single Asp718 site. In the final step, the tsr gene was inserted as a 1.8 kb BamHI fragment into the single BamHI site of this construct.

Plasmid pMOV181 was derived from pMOV40 by replacing the hyg gene with the agarase gene (dag) from *S. coelicolor* derived from pMT605 (Kendall and Cullum (1984) *Genet. Res.* 51, 71–74) and by exchanging the tsr gene with a copy of the hyg gene. Plasmid pMOV203 was constructed in a first step by introducing a 3.1 kb BclI fragment from pIJ486 (Ward et al. (1986) *Mol. Gen. Genet.* 203, 466–478) containing the origin of replication of pIJ101 into the BglII site of pSP72 (Promega). In a second step, the hyg gene was inserted as a 1.45 kb HindIII fragment into the single HindIII site.

Isolation and Manipulation of DNA and RNA

Plasmid DNA was isolated from *E. coli* by an alkaline lysis procedure (Sambrook et al. (1989) *Molecular Cloning, A laboratory manual*, Cold Spring Harbor, N.Y., Cold Spring Harbor Laboratory Press). The isolation of plasmid DNA, total DNA and RNA from Streptomyces was as described (Hopwood et al. (1985) supra). DNA fragments were isolated by separation in low melting temperature agarose and purified by phenol extraction and ethanol precipitation. Manipulations of DNA were as described (Sambrook et al. (1989) supra). Restriction endonucleases and DNA modifying enzymes were obtained from various commercial suppliers and used according to the instructions of the vendor.

Southern and Northern Blots

DNA fragments were separated by horizontal agarose gel electrophoresis in TAE-buffer and immobilized on Hybond N membranes (Amersham) as described (Sambrook et al. (1989) supra). RNA was separated in agarose/formaldehyde gels according to Sambrook et al. (1989) supra), and transferred to Hybond N membranes. The conditions for both Southern and Northern blot hybridizations were as described (Church and Gilbert (1984) *Proc. Natl. Acad. Sci. USA* 81, 1991–1995). Labeled DNA fragments as probes for hybridization experiments were generated using a multiprime DNA labeling kit (Amersham) according to the supplier's specifications.

DNA Sequence Analysis

Defined restriction endonuclease-generated DNA fragments were cloned on M13mp18 (Norrander et al. (1983) *Gene* 26, 101–106), and the sequence of both strands determined by the chain termination procedure using a DNA sequencing kit (U.S. Biochemical). Sequence analyses were performed using the GCG Sequence Analysis Software package.

Site-Directed Mutagenesis

DNA sequences were mutated according to the method of Kunkel et al. (1987) *Methods Enzymol.* 154, 367–382). The mutagenic oligodeoxynucleotide to change the anticodon region of the tRNA$^{Tyr}$ gene had the sequence (SEQ ID No: 4) 5'-GCCGGCAGATCT-GCAGTCTGCTCCC-3'.

Gene Replacement

DNA fragments of regions to be altered were cloned in *E. coli* on pUC19 carrying either the tsr gene or the hyg gene for use as selective marker in Streptomyces. After manipulation of the insert DNA in vitro, the constructs, which lack the ability to replicate in Streptomyces, were introduced into *S. lividans* and transformant clones expressing resistance to tsr or hyg, and consequently containing the pUC-based construct integrated into the host chromosome, were selected. After non-selective growth for two consecutive cycles of sporulation, resolution of the non-tandem direct repeat was monitored by marker loss in replica plating experiments. Mutant clones were detected by analysis of the genomic DNA by Southern blot hybridization.

Results

Deletion of the Chromosomal SLP1 attB Sequence From *S. lividans*

SLP1 normally integrates at a single site (i.e. attB) in the chromosome of *S. lividans*. Prior to undertaking the deletion of the attB locus, we carried out preliminary experiments designed to assess the efficiency of the gene replacement procedure described in Experimental Procedures. Integration vectors derived from the *E. coli* replicon pBE1 and consequently lacking the ability to replicate in Streptomyces were introduced by transformation into *S. lividans* TK21 to introduce an insertion mutation into the afsR locus, which previously has been implicated in the synthesis of pigmented antibiotics by *S. lividans*. With 5.3 kb and 2.7 kb regions of homology with the host chromosome flanking the foreign DNA segment cloned on the integrating plasmid and a foreign DNA segment up to 1.6 kb in length, we observed integration frequencies of $0.1-2.0 \times 10^{2}$/µg of plasmid DNA. Non-selective growth of these integrants yielded clones that had lost the marker gene of the plasmid at a frequency ranging from 1 to 10%. Among these clones, replacement of the wild type chromosomal locus with the mutated one was found by Southern blot hybridization to occur reproducibly by homologous recombination at a frequency of 25% or higher. Because of the observed high frequency of gene replacement in *S. lividans* only a limited number of clones is required for detection of recombinant clones; we concluded that the gene replacement procedure is a practical means of introducing mutations that do not result in detectable phenotypic changes at specific chromosomal sites.

To delete the attB locus of *S. lividans* TK21, we introduced pMOV75, a plasmid carrying an EcoRI/HindIII DNA fragment that spans the attB region but contains a 960 bp deletion of attB and the nearby flanking sequences (Table 1). Clones that contained chromosomally integrated pMOV75 were isolated by selecting for the thiostrepton (tsr) resistance determinant carried by the plasmid, which is incapable of replication in *S. lividans*, and were subsequently screened-after two cycles of sporulation in the absence of selection-for the loss of tsr resistance by resolution of the chromosomal duplication. Genomic DNA isolated from each clone was examined by Southern blot hybridization for replacement of the intact attB locus by the DNA segment harboring a deletion in attB. In all 75 clones, the wild type DNA configuration at the attB locus had been retained and in no instance was deletion of attB observed.

As the desired recombinant was not detected by Southern blotting in the above experiment, a phenotypic marker was used to assess the frequency at which recombinants at the *S. lividans* attB locus were generated. The *S. coelicolor* dag gene, which encodes an enzyme that digests agar and leads to depression in the agar surrounding growing colonies that express the gene, was substituted for the attB site of a *S. lividans* chromosomal DNA fragment cloned on pMOV72. Following the gene replacement procedure, frequency of dag⁺ colonies was assessed; all clones that had lost the tsr marker gene had the wild type phenotype (e.g. were dag⁻), indicating that the wild type attB site had not been replaced by the allele mutated by insertion of the dag gene.

Figure 1:
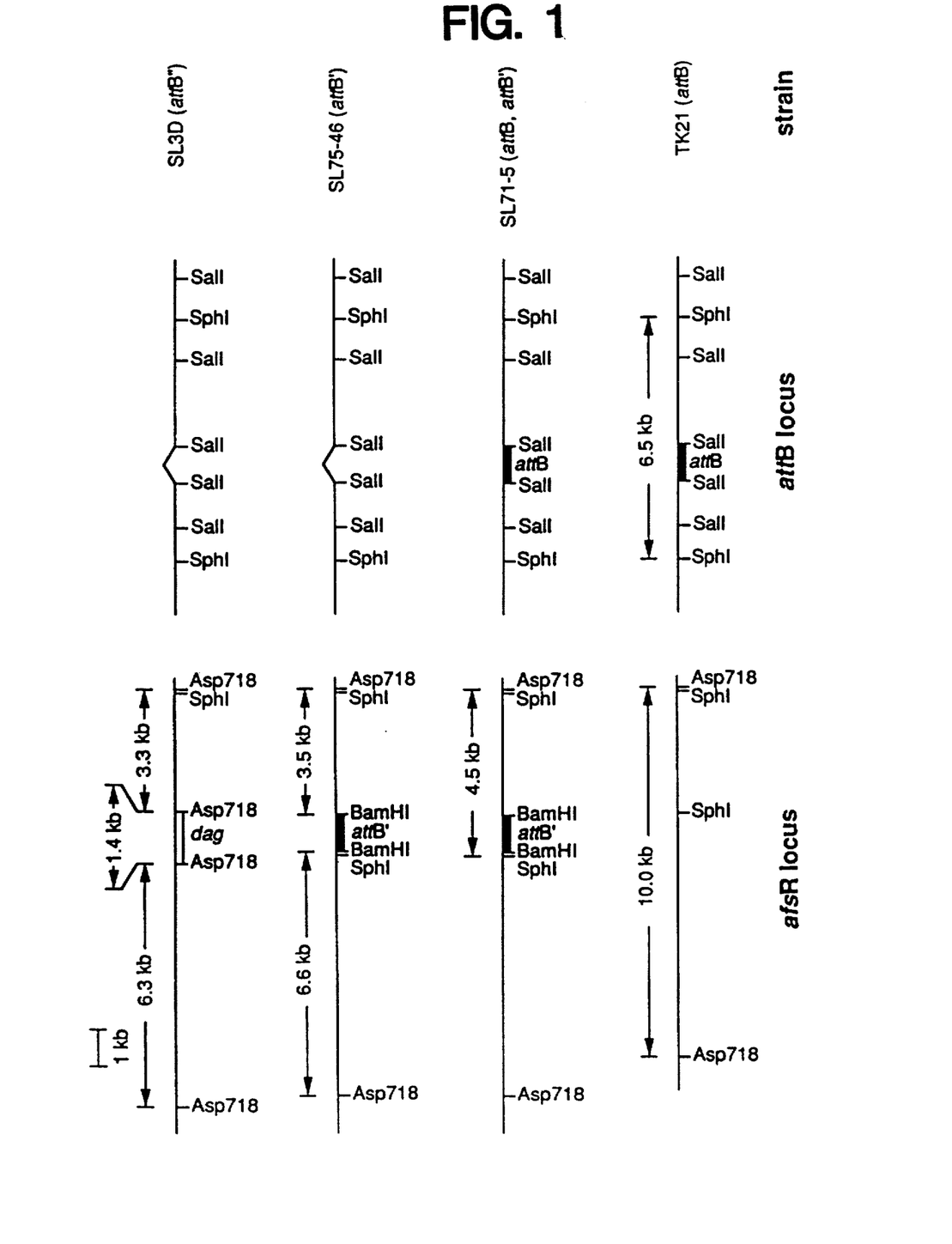
FIG. 1 is a DNA restriction map of the chromosomal attB and afsR loci of *S. lividans* TK21 and certain mutant strains. The location of the 960 bp attB-containing DNA fragment is shown by a closed bar. The position of the dag gene is shown by an open bar. DNA deletions are indicated by a V-shaped structure. The sizes of relevant DNA fragments are indicated to aid the interpretation of Southern blots.

To determine whether the attB sequence, which was refractory to gene replacement in the above experiments, could be deleted from the *S. lividans* chromosome if a secondary attB site is provided, we constructed a strain containing two chromosomal attB sites, using pMOV71 to insert a copy of attB at the afsR locus (Table 1). We refer to this additional copy of attB as attB' and to the strain that carries it as SL71-5 (FIG. 1). After demonstrating that the ancillary attB' locus can function in both the integration and excision of SLP1, we undertook again to delete the primary attB site by the gene replacement procedure, using pMOV75 as the integrative vector. One out of 20 clones analyzed by Southern blotting after resolution of the chromosomal duplication had deleted attB from the chromosome. This mutant strain lacking attB but containing attB' was designated SL75-46; a map of the relevant regions of its chromosomes is shown in FIG. 1.

Similarly, the adventitious attB' locus inserted within the afsR gene region could be deleted by pMOV40-directed gene replacement from the chromosome of strain SL71-5 carrying the primary attB site. The frequency of clones showing phenotypic evidence of deletion of the secondary attB' locus in the presence of attB was 37% (69 of 188 thiostrepton sensitive clones that had resolved the chromosomal duplication in the gene replacement procedure were resistant to hygromycin); deletion of attB' was specifically confirmed in all of 12 individual clones that were selected randomly from this batch for further testing by Southern blotting. The 37% frequency of deletion of attB' observed in cells that contain attB contrasts with the 5% frequency of deletion of attB in attB'-containing cells. Because of the higher frequency of gene replacement found at the afsR locus, we used strain SL75-46 for further experiments.

When deletion of attB' was attempted by the introduction of pMOV40 into SL75-46, which lacks attB (FIG. 1), all 84 clones that had lost the tsr marker gene of the plasmid construct were found to have reverted to the wild type phenotype (e.g. were hygs). This phenotypic reversion was shown by Southern blotting of DNA from several randomly selected integrants to have occurred by homologous recombination between sequences of the non-tandem chromosomal duplication of the afsR gene region that results from integration of pMOV40. Given the high frequency of deletion of the attB' site in cells carrying attB, our inability to delete attB' from cells that lack the attB locus strongly suggested that the attB locus encodes a function essential to *S. lividans*.

Figure 2:
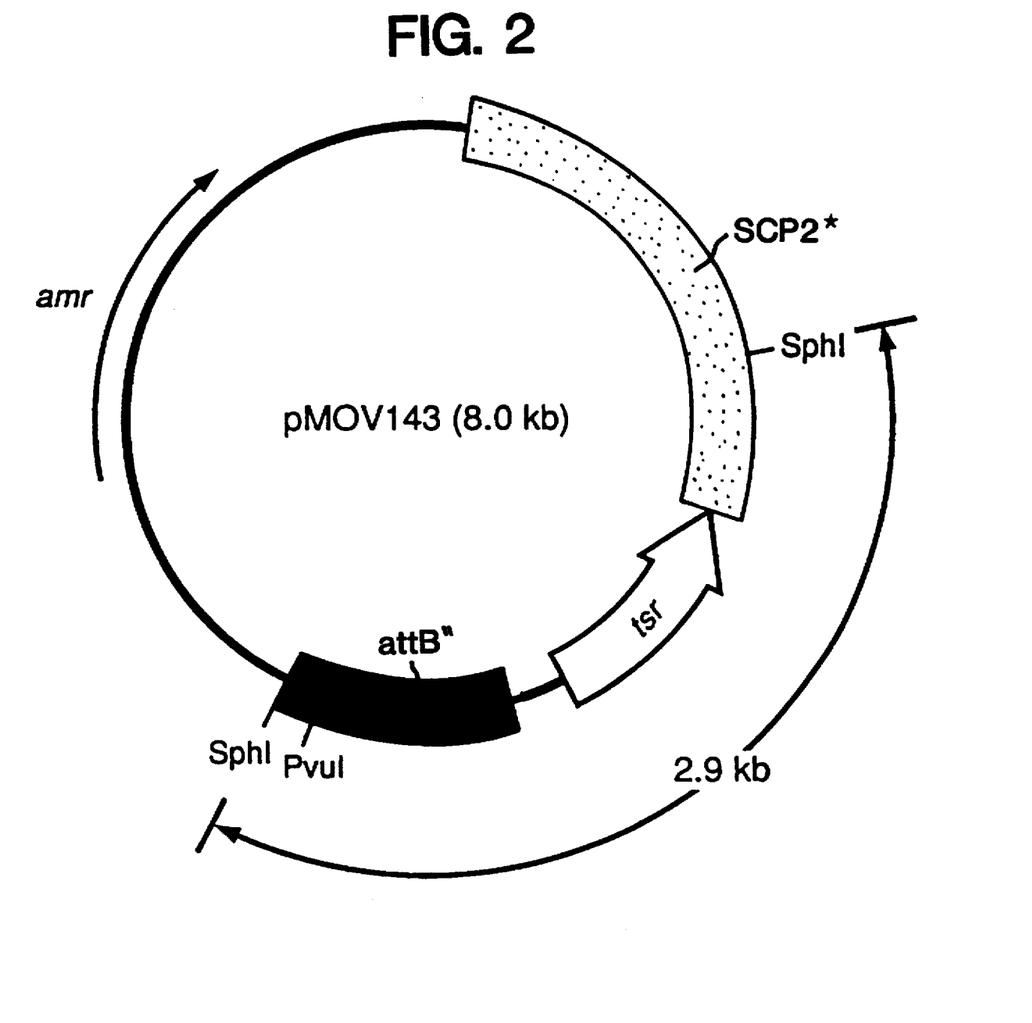
FIG. 2 is a map of plasmid pMOV143. The attB"-containing DNA segment was introduced into the single PstI site of pOJ160. Sequences of Streptomyces origin are shown by bars or by an open arrow. The position of the two SphI sites bracketing a 2.9 kb DNA fragment is shown. The PvuI site within attB" determines the fragment orientation (see FIG. 3) and is not unique on the plasmid. As the original plasmid pOJ160, plasmid pMOV143 has a copy number of 1–2 per genome. SCP2*: minimal replicon of SCP2*; tsr: thiostrepton resistance gene; attB": attB-containing DNA fragments; amr: apramycin resistance gene.

This notion was further tested, and the trans-acting capabilities of the putative essential function investigated, by determining whether the primary attB' locus of SL75-46 can be deleted when the 960 bp attB-complementing sequence is provided extrachromosomally on a plasmid. For these experiments, the 960 bp DNA segment was inserted as a PstI fragment onto pOJ160 (available from B. Schoner) to yield pMOV143 (FIG. 2); the attB sequence on pMOV143, which also contains a tsr gene that can be used to select transformants carrying the plasmid, is designated attB".

Plasmids pMOV143 and pMOV181, a hygromycin-resistance construct containing a dag gene insert in the afsR sequence, were introduced by cotransformation into strain SL75-46, which lacks attB as described above. By growing the initial tsr-resistant and hyg-resistant transformants in the absence of hygromycin, hyg-sensitive derivatives were obtained; among 100 individual clones analyzed, 67 (67%) were dag⁺. Southern blot analysis of total DNA from 12 of these clones using the dag-containing insert DNA of pMOV181 as a probe showed that in all instances replacement of the chromosomal attB' locus by the dag gene had occurred. One (1) µg samples of total DNA from the indicated strains were cleaved by Asp718 and BamHI, electrophoresed in 0.6% agarose, blotted onto membranes, and probed to 32P-labeled insert DNA of pMOV181.

Samples of sized known DNA were concurrently run for size determinations. A map of the relevant chromosomal regions for one of these strains, SL3D, is shown in FIG. 1. Probing with the 960 bp attB-containing DNA fragment showed adventitious hybridizing sequences in addition to the expected 2.9 kb Sphl fragment of pMOV143 (FIG. 2) for all except one of these isolates (strain SL3D), suggesting that plasmid DNA rearrangement had occurred; the DNA configuration of pMOV143 in strain SL3D was constant in the region analyzed in each of 12 subclones examined by Southern blotting. As seen in Table 2, pMOV143, a derivative of a plasmid (SCP2,) that previously has been shown to be lost rapidly from clonal populations of dividing cells grown in the absence of selection (Bibb et al. (1980) *Gene* 30, 157–166; Kendall and Cullum (1988) *Genet. Res.* 51, 71–74), was uniformly maintained without external selection in SL3D, which lacks any chromosomal copy of attB. In contrast, the pMOV143 plasmid was not stably inherited in strain SL75-46, which contains attB' in its genome.

TABLE 2

Stability of plasmid pMOV143 in *S. lividans* SL75-46 and SL3D.

| Strain | tsr$^r$ Colonies/ Total Colonies Tested | Loss of Plasmid pMOV143 (%) |
|---|---|---|
| SL75-46 | 0/184 | 100 |
| SL3D | 180/180 | 0 |

A single colony of the indicated strains containing pMOV143 was selected and grown for one life cycle on agar plates containing thiostrepton. Spores from these strains were plated for single colonies on non-selective agar media and the frequency of plasmid loss determined by replica plating onto selective agar plates.

The Nucleotide Sequence of the attB Locus

Figure 3A:
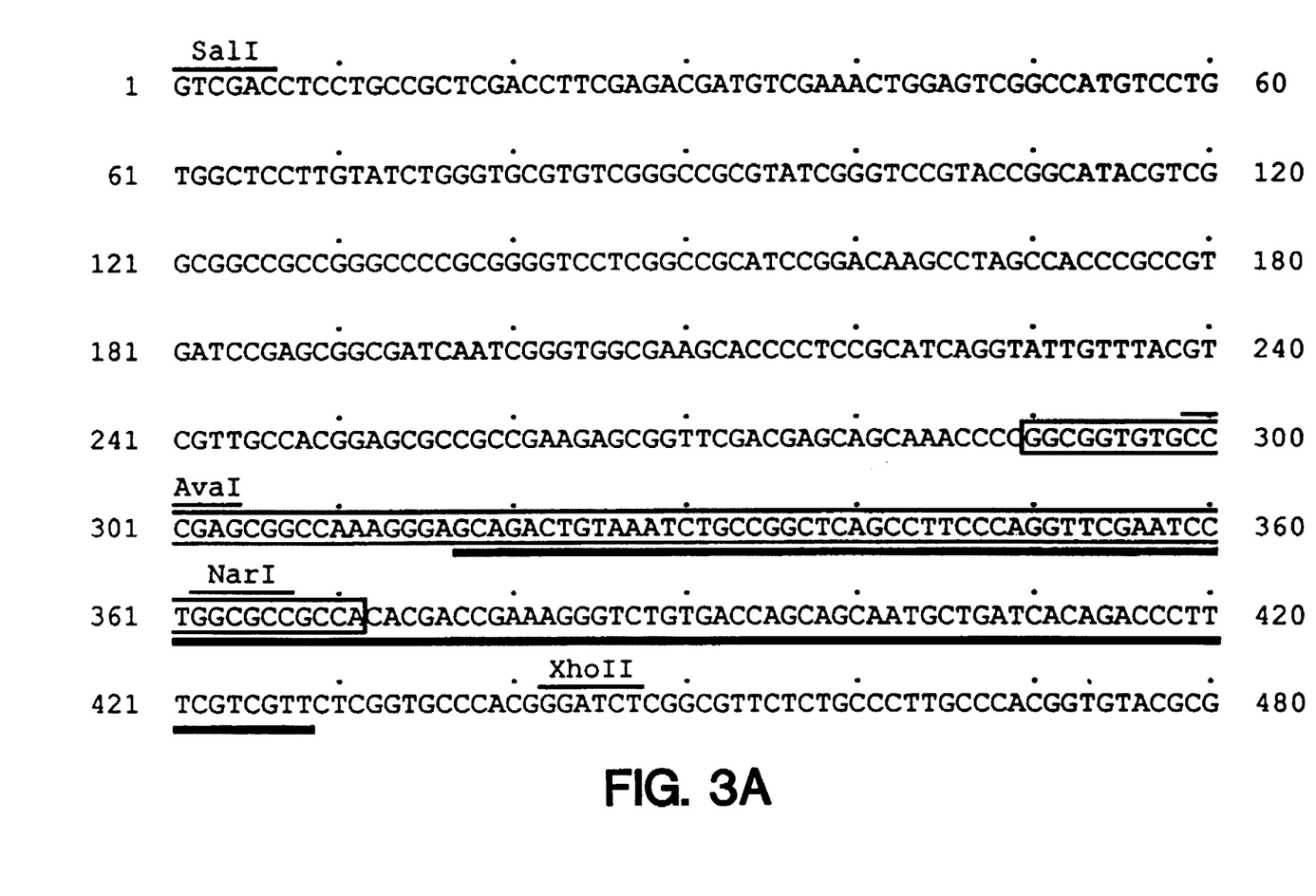
FIG. 3 is a nucleotide sequence (SEQ ID No: 1) of the 958 bp SalI DNA fragment from S. lividans TK21 containing the chromosomal attB site of SLP1. The structural tRNA$^{Tyr}$ gene is boxed. The attB sequence is underlined. The DNA sequence shows the non-coding strand for the tRNA$^{Tyr}$ gene that corresponds to the tRNA transcription.
Figure 3B:
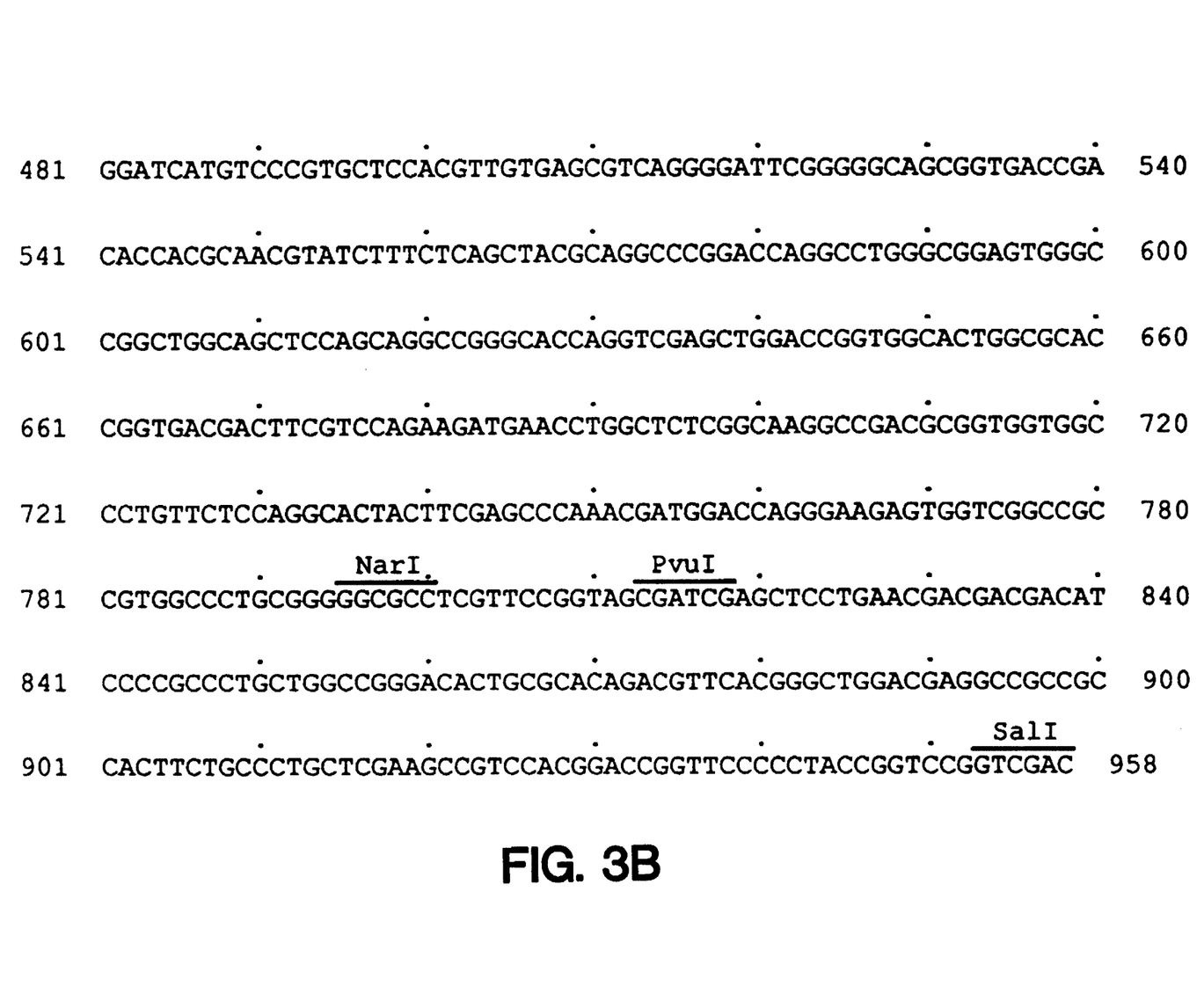
Figure 4:
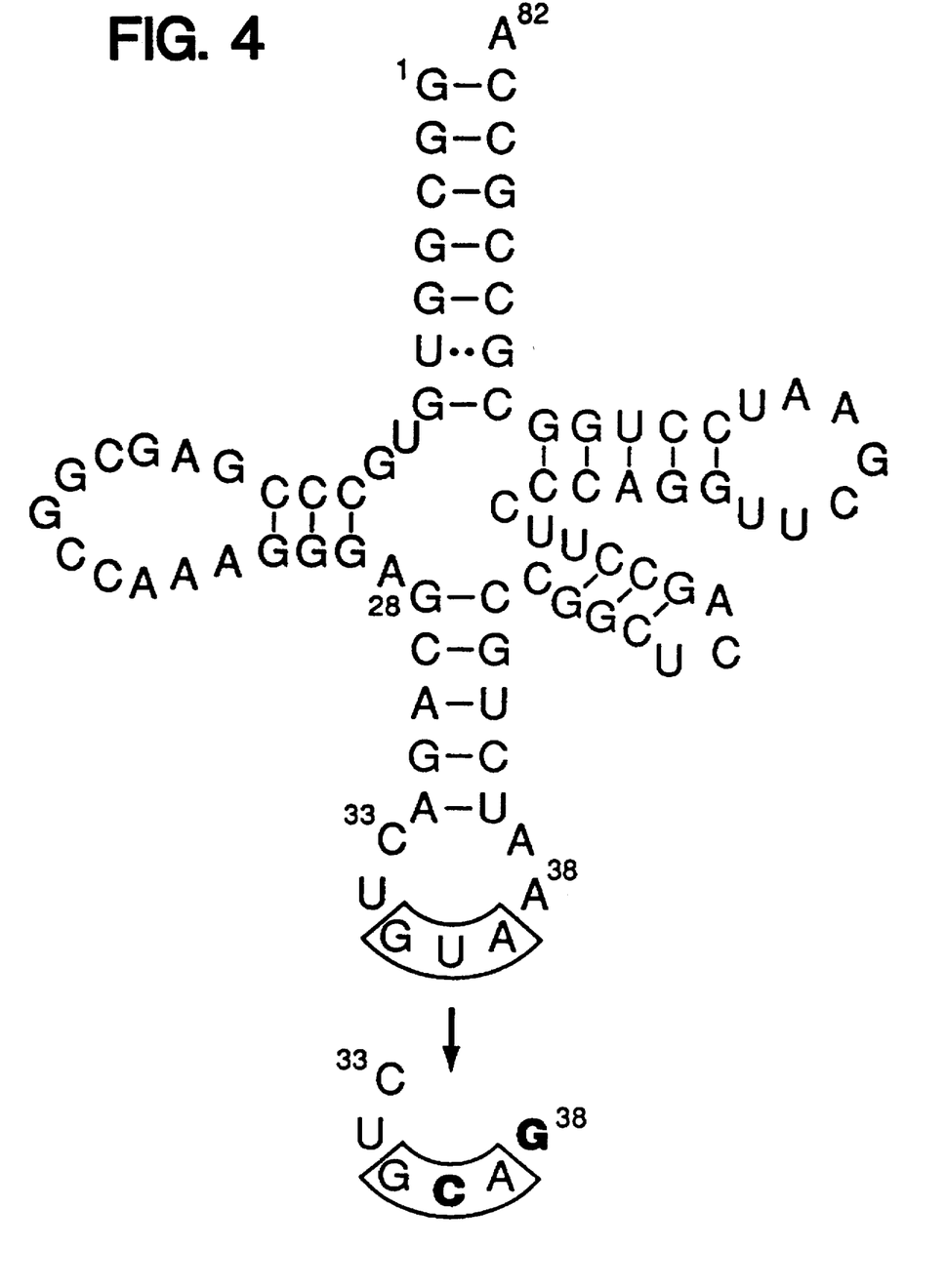
FIG. 4 is the deduced secondary structure of the tRNA$^{Tyr}$ (SEQ ID Nos: 2 and 3). Nucleotide changes introduced by oligonucleotide-directed mutagenesis at position 36 and 38 are shown in bold and generate a PstI site (pos. 33–38). The boxes indicate the anticodon of the wild type and mutant tRNA. The G residue at position 28 corresponds to the 5' end of the SLP1 attP sequence.

To investigate further the essential function encoded by the 960 bp DNA fragment, we sequenced the entire fragment. A series of restriction endonuclease-generated DNA fragments were introduced in both orientations into a bacteriophage M13 vector and the nucleotide sequence of each subcloned fragment was determined by chain termination as indicated above (FIG. 3). Screening of the GCG data base for homology with the sequence showed substantial similarity to tRNA$^{Tyr}$ genes cloned from a variety of different species (Goodman et al. (1970) supra; Hollingsworth and Hallick (1982) supra; Weisshaar et al. (1990) supra). Part of the sequence that encodes what appears to be a full length tRNA$^{Tyr}$ species was determined earlier (Omer and Cohen (1986) supra), and was observed by Reiter et al. (1989), *Nucleic Acids Res.* 17, 1907–1914, to include a cloverleaf secondary structure characteristic of tRNAs, as shown in FIG. 4. This segment is boxed in FIG. 3. In addition, an ORF of 142 codons that shows the third codon position bias characteristic of Streptomyces genes (Bibb et al. (1984) *Gene* 30, 157–166) proceeds rightward in FIG. 3 from a potential GTG start codon at nucleotide position 533–535. This ORF, which extends beyond the fragment sequenced, has no similarity to protein-encoding sequences of previously cloned genes.

Transcript Analysis

Total RNA was isolated from cultures of *S. lividans* TK21 grown in liquid media for various periods of time (24 h, 36 h, 48 h, 60 h, 120 h). Twenty (20) μg amounts were electrophoresed in 1.5% agarose containing 6% formaldehyde, blotted, and probed to a $^{32}$P-labeled 440 bp attB-containing fragment (SalI (pos. 1)-XhoII (pos. 442), FIG. 3). A single transcript having the same electrophoretic mobility as tRNA and 5S ribosomal RNA was detected by the attB-containing DNA probe. Only the same single transcript was detected when these RNA samples were probed with the entire 960 bp attB sequence.

The tRNA$^{Tyr}$ Gene is Functional and Essential for Viability of *S. lividans*

To demonstrate directly that the tRNA$^{Tyr}$ gene sequence found on the transcript-encoding 960 bp SalI fragment specifies the function essential for viability of *S. lividans*, we altered the deduced anticodon segment of the tRNA gene. The 440 bp SalI-XhoII DNA fragment (position 1-442(SEQ ID: No: 1), FIG. 3) was introduced in *E. coli* on M13mp18 and the sequence of the presumed anticodon region was mutated by oligonucleotide-directed mutagenesis as described above. The mutations made replace the Tyr anticodon (GUA) with one specific for Cys (GCA), and concurrently introduce a cleavage site for PstI (FIG. 4) (SEQ ID Nos: 2 and 3). The entire fragment was resequenced following mutagenesis to ensure that no other change occurred during the manipulations, and then was ligated to the unmutagenized 520 bp XhoII-SalI DNA fragment (position 442-953, (SEQ ID No: 1) FIG. 3) to reconstitute the 960 bp SalI DNA fragment. DNA segments spanning various regions of the reconstituted and the wild type 960 bp fragment were inserted as BamHI fragments into pMOV203 to generate the plasmids pMOV204 to pMOV208 (FIG. 5), which were then introduced by transformation into strain SL3D.

As shown in Table 3, the tsr marker of the unstable pMOV143 plasmid was lost from the host cell at a frequency of 100% during two cycles of sporulation in the absence of selection when the incoming plasmid carried a DNA fragment having a wild type copy of the tRNA$^{Tyr}$ gene (e.g. pMOV204 and pMOV206), but was uniformly maintained in the spore population when pMOV203, which lacks any attB insert, was introduced; the physical presence or absence of pMOV143 was confirmed in these experiments by Southern blot hybridization. Unexpected however was the loss of pMOV143 in instances where the tRNA gene on the incoming plasmid contained a mutated anticodon region (pMOV207 and pMOV208) or was deleted for a 210 bp DNA segment that includes the entire tRNA$^{Tyr}$ coding sequence (i.e. pMOV205).

TABLE 3

Stability of attB"-containing pMOV143 plasmid in *S. lividans* SL3D transformed with plasmids carrying a wild type or mutant attB site.

| Incoming Plasmid | tsr$^r$ Colonies/ Total Colonies Tested | Loss of Resident Plasmid pMOV143 (%) |
|---|---|---|
| pMOV203 | 105/105 | 0 |
| pMOV204 | 0/104 | 100 |
| pMOV205 | 10/18 | 44 |
| pMOV206 | 0/102 | 100 |
| pMOV207 | 59/104 | 43 |
| pMOV208 | 43/103 | 58 |

Figure 5:
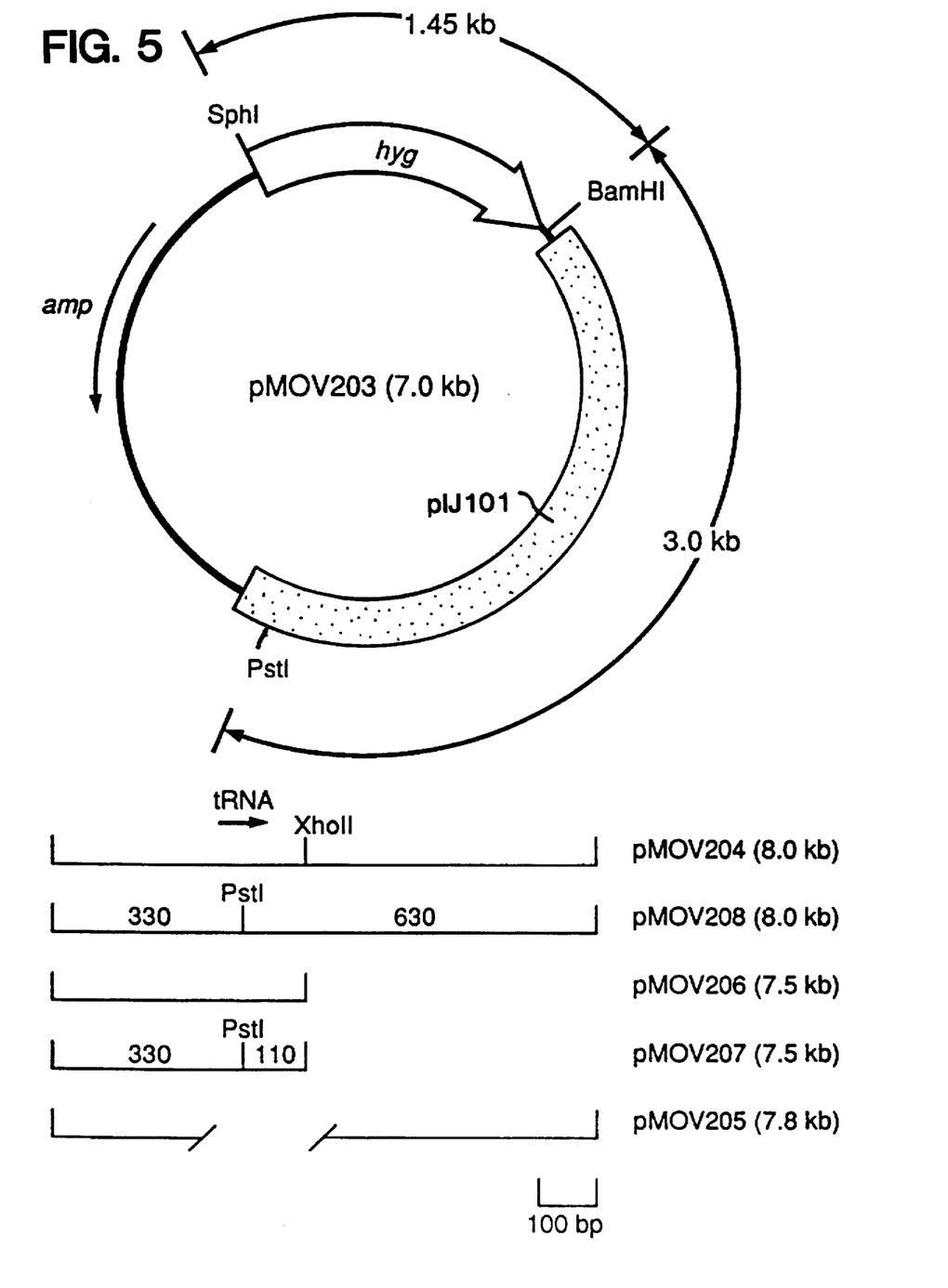

*S. lividans* SL3D, which lacks a chromosomal copy of attB but includes as a resident plasmid pMOV143, which contains attB" and a tsr gene, was transformed separately by each of the indicated plasmids carrying a hyg resistance determinant. A map of the incoming plasmids is shown in FIG. 5. Transformants selected solely for the incoming plasmid were grown for one additional life cycle on agar media containing hygromycin. The frequency of loss of plasmid pMOV143 was assessed by replica plating onto selective agar media containing thiostrepton.

Southern blot hybridization analysis of total genomic DNA from four thiostrepton-sensitive clones derived from isolates that had been transformed earlier with each of the plasmids pMOV205, pMOV207, and pMOV208 provided both an explanation for the observed result and confirmation that the tRNA$^{Tyr}$ sequence encodes the essential function carried by the 960 bp SalI DNA fragment. Total DNA (1 μg)

cut by SphI and PstI was separated by electrophoresis in 0.7% agarose, blotted, and probed to riP-labeled 960 bp attB-containing DNA fragment. The plasmid constructs are indicated above. In all of the analyzed clones, the PstI site generated by mutation of the tRNA$^{Tyr}$ anticodon region of pMOV207 and pMOV208 (FIG. 8) was now absent. Similarly, by introducing construct pMOV205, in which the entire coding region of the tRNA gene had been deleted, the deletion was replaced by the wild type sequence, indicating strong selective pressure for the intact tRNA$^{Tyr}$ gene.

It is evident from the above results, that by use of an essential tRNA gene in a tRNA$^-$ background, many advantages ensue for the expression of an exogenous protein. The small size of the tRNA is very convenient for manipulation and provides for a low probability of integration into the chromosome. Furthermore, one can maintain single or oligocopy plasmids in the host, so that one may have multiple copies of the exogenous gene encoding the protein of interest present in the expression host. Selective medium is not required, since the absence of the essential tRNA results in rapid mortality of any cells which loose the plasmid. Thus, the cells comprising the plasmid are not compromised in their growth characteristics and can be fully active. Furthermore, by employing the subject approach, namely inactivating a particular tRNA and making the tRNA available on a plasmid, one can use commercially-available organisms which have found use in fermentation, and modify them to stabilize the plasmid, without adversely affecting their desirable properties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An expression system for producing an exogenous protein in a prokaryotic host, the system comprising:

a secretory prokaryotic host having a negative background for an essential tRNA specific for an amino acid, and a plasmid having an origin of replication, a functional gene for a tRNA specific for said amino acid, and a structural gene of interest which when present in said host is expressed.

2. An expression system according to claim 1, wherein said prokaryotic host is a member of the family actinomycetaceae.

3. An expression system according to claim 2, wherein said prokaryotic host is a Streptomyces.

4. An expression system according to claim 1, wherein said amino acid is tyrosine.

5. A plasmid comprising: an origin of replication unstably maintained in a prokaryotic host; a gene encoding an essential tRNA specific for an amino acid; and a structural gene of interest, which when present in said host is transcribed.

6. A plasmid according to claim 5, wherein said prokaryotic host is a member of the family actinomycetaceae.

7. A plasmid according to claim 6, wherein said prokaryotic host is a Streptomyces.

8. A plasmid according to claim 7, wherein said amino acid is tyrosine.

9. A plasmid according to claim 6, wherein said amino acid is tyrosine.

10. A method for producing an exogenous protein in a prokaryotic host, said method comprising:

growing a prokaryotic host in a non-selective medium, wherein said host lacks an essential tRNA for a particular amino acid and comprises a plasmid unstably maintained in said host, said plasmid comprising:

an origin of replication unstably maintained in said host; a gene encoding an essential tRNA specific for said amino acid, which gene is transcribed in said host; and a structural gene encoding a protein of interest which gene when present in said host is expressed, whereby said protein of interest is produced; and isolating said protein of interest.

11. A method according to claim 10, wherein said prokaryotic host is a member of the family actinomycetaceae.

12. A method according to claim 11, wherein said prokaryotic host is a Streptomyces.

13. A method according to claim 10, wherein said amino acid is tyrosine.

14. A method according to claim 10, wherein said amino acid is tyrosine.

* * * * *

UNITED STATES PATENT AND TRADEMARK OFFICE
CERTIFICATE OF CORRECTION

PATENT NO.   : 5,607,842
DATED        : March 4, 1997
INVENTOR(S)  : Stanley N. Cohen, et. al.

It is certified that error appears in the above-identified patent and that said Letters Patent is hereby corrected as shown below:

Column 1, line 9, insert the following:

--This invention was made with Government support under grant no. AI08618 awarded by the National Institutes Of Health, and grant no. MV-44Q by the American Cancer Society.---

Signed and Sealed this

Ninth Day of March, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 958 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:1:

```
GTCGACCTCC  TGCCGCTCGA  CCTTCGAGAC  GATGTCGAAA  CTGGAGTCGG  CCATGTCCTG    60
TGGCTCCTTG  TATCTGGGTG  CGTGTCGGGC  CGCGTATCGG  GTCCGTACCG  GCATACGTCG   120
GCGGCCGCCG  GGCCCCGCGG  GGTCCTCGGC  CGCATCCGGA  CAAGCCTAGC  CACCCGCCGT   180
GATCCGAGCG  GCGATCAATC  GGGTGGCGAA  GCACCCCTCC  GCATCAGGTA  TTGTTTACGT   240
CGTTGCCACG  GAGCGCCGCC  GAAGAGCGGT  TCGACGAGCA  GCAAACCCCG  GCGGTGTGCC   300
CGAGCGGCCA  AAGGGAGCAG  ACTGTAAATC  TGCCGGCTCA  GCCTTCCCAG  GTTCGAATCC   360
TGGCGCCGCC  ACACGACCGA  AAGGGTCTGT  GACCAGCAGC  AATGCTGATC  ACAGACCCTT   420
TCGTCGTTCT  CGGTGCCCAC  GGGATCTCGG  CGTTCTCTGC  CCTTGCCCAC  GGTGTACGCG   480
GGATCATGTC  CCGTGCTCCA  CGTTGTGAGC  GTCAGGGGAT  TCGGGGCAG   CGGTGACCGA   540
CACCACGCAA  CGTATCTTTC  TCAGCTACGC  AGGCCCGGAC  CAGGCCTGGG  CGGAGTGGGC   600
CGGCTGGCAG  CTCCAGCAGG  CCGGGCACCA  GGTCGAGCTG  GACCGGTGGC  ACTGGCGCAC   660
CGGTGACGAC  TTCGTCCAGA  AGATGAACCT  GGCTCTCGGC  AAGGCCGACG  CGGTGGTGGC   720
CCTGTTCTCC  AGGCACTACT  TCGAGCCCAA  ACGATGGACC  AGGGAAGAGT  GGTCGGCCGC   780
CGTGGCCCTG  CGGGGGCGCC  TCGTTCCGGT  AGCGATCGAG  CTCCTGAACG  ACGACGACAT   840
CCCCGCCCTG  CTGGCCGGGA  CACTGCGCAC  AGACGTTCAC  GGGCTGGACG  AGGCCGCCGC   900
CACTTCTGCC  CTGCTCGAAG  CCGTCCACGG  ACCGGTTCCC  CCTACCGGTC  CGGTCGAC    958
```

( 2 ) INFORMATION FOR SEQ ID NO:2:

( i ) SEQUENCE CHARACTERISTICS:
    ( A ) LENGTH: 82 base pairs
    ( B ) TYPE: nucleic acid
    ( C ) STRANDEDNESS: both
    ( D ) TOPOLOGY: unknown ( i i ) MOLECULE TYPE: tRNA ( x i ) SEQUENCE DESCRIPTION: SEQ ID NO:2:

```
GGCGGUGUGC CCGAGCGGCC AAAGGGAGCA GACUGUAAAU CUGCCGGCUC AGCCUUCCCA        60
GGUUCGAAUC CUGGCGCCGC CA                                                82
```

( 2 ) INFORMATION FOR SEQ ID NO:3:

( i ) SEQUENCE CHARACTERISTICS:
    ( A ) LENGTH: 82 base pairs
    ( B ) TYPE: nucleic acid
    ( C ) STRANDEDNESS: both
    ( D ) TOPOLOGY: unknown ( i i ) MOLECULE TYPE: tRNA ( x i ) SEQUENCE DESCRIPTION: SEQ ID NO:3:

```
GGCGGUGUGC CCGAGCGGCC AAAGGGAGCA GACUGCAGAU CUGCCGGCUC AGCCUUCCCA        60
GGUUCGAAUC CUGGCGCCGC CA                                                82
```

( 2 ) INFORMATION FOR SEQ ID NO:4:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

```
GCCGGCAGAT CTGCAGTCTG CTCCC                                             25
```